(12) United States Patent
Bornemann

(10) Patent No.: US 9,321,013 B2
(45) Date of Patent: Apr. 26, 2016

(54) ARTIFICIAL "ARTERIO-VENOUS" PERMEABLE HOLLOW FIBER CAPILLARY SYSTEM

(76) Inventor: Reinhard Bornemann, Bielefeld (DE)

( * ) Notice: Subject to any disclaimer, the term of this patent is extended or adjusted under 35 U.S.C. 154(b) by 1725 days.

(21) Appl. No.: 11/900,109

(22) Filed: Sep. 10, 2007

(65) Prior Publication Data

US 2009/0196855 A1 Aug. 6, 2009

(30) Foreign Application Priority Data

Sep. 12, 2006 (DE) .......................... 10 2006 042 732

(51) Int. Cl.
| | | |
|---|---|---|
| *A61K 35/36* | (2015.01) | |
| *B01D 63/02* | (2006.01) | |
| *A61M 1/00* | (2006.01) | |
| *A61M 3/02* | (2006.01) | |
| *A61M 27/00* | (2006.01) | |

(52) U.S. Cl.
CPC ............. *B01D 63/02* (2013.01); *A61M 1/0084* (2013.01); *A61M 1/0088* (2013.01); *A61M 3/0283* (2013.01); *A61M 27/00* (2013.01); *B01D 63/026* (2013.01)

(58) Field of Classification Search
None
See application file for complete search history.

(56) References Cited

U.S. PATENT DOCUMENTS

| | | | | |
|---|---|---|---|---|
| 4,578,191 A | * | 3/1986 | Jaffrin et al. ................ | 210/323.2 |
| 5,262,055 A | * | 11/1993 | Bae et al. ...................... | 210/645 |
| 5,549,674 A | * | 8/1996 | Humes et al. .............. | 623/23.65 |
| 5,656,372 A | * | 8/1997 | Gentile et al. ................ | 428/376 |
| 5,681,568 A | * | 10/1997 | Goldin et al. .............. | 424/184.1 |
| 6,627,422 B1 | * | 9/2003 | Li et al. .......................... | 435/182 |
| 6,922,643 B2 | * | 7/2005 | Takakamo et al. .............. | 702/58 |
| 7,019,545 B2 | * | 3/2006 | Kang et al. .................... | 324/765 |

OTHER PUBLICATIONS

Pangrle et al. "Investigation of Fluid Flow Patterns in a Hollow Fiber Module Using Magnetic Resonance Velocity Imagining" Biotechnology Techniques, vol. 3, No. 1, pp. 67-72 (1989).*
Merriam-Webster.com, "Proximate", 4 pages, accessed at http://www.merriam-webster.com/dictionary/proximate on Jun. 4, 2015.*
Cabodi et al. "An Active Wound Dressing for Controlled Convective Mass Transfer With the Wound Bed" Journal of Biomedical Materials Research Part B: Applied Biomaterials, Jul. 2007;82(1):210-22.*
Plettig et al. "Feasibility study of an active wound dressing based on hollow fiber membranes in a porcine wound model" Burns 4 1 ( 2 0 1 5 ) 778-788.*
E.H. Nicollian and J.R. Brews, "Avalanche Breakdown and Tunneling," MOS (Metal Oxide Semiconductor) Physics and Technology, Wiley-Interscience, 1981, p. 378.

* cited by examiner

Primary Examiner — Thane Underdahl

(57) ABSTRACT

An artificial "arterio-venous" permeable hollow fiber capillary membrane system for wound treatment is described. The capillary membrane system can be placed onto a wound or under the wound dressing to enable fluid/mass exchange, in turn allowing the regulation of pH and electrolyte levels, the supply of factors/mediators/medications, the removal of secretion and waste material, and the support of therapeutically applied cells in the wound.

17 Claims, 9 Drawing Sheets

Fig. 3a
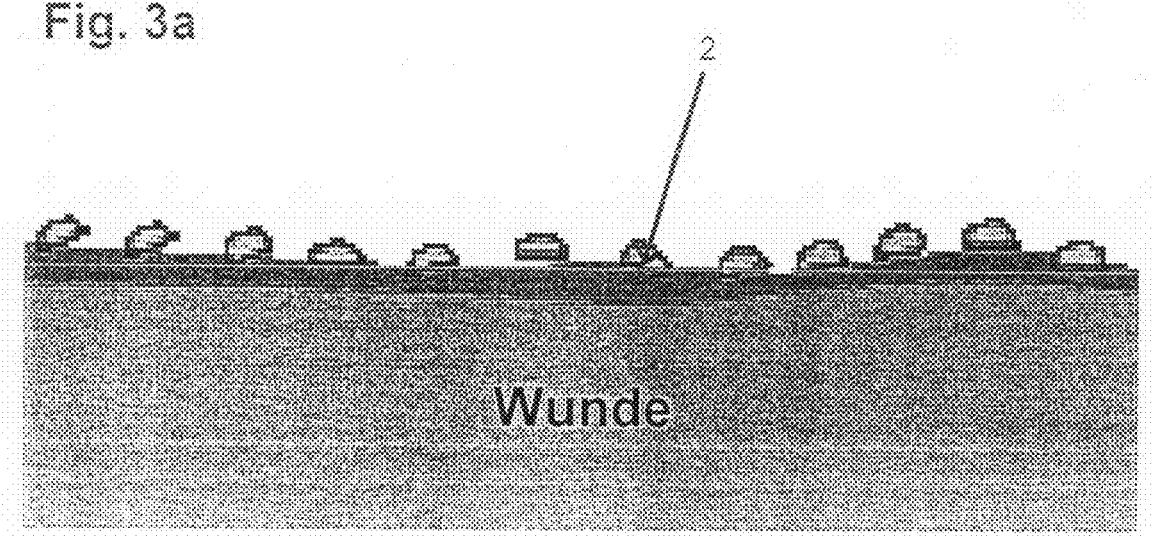
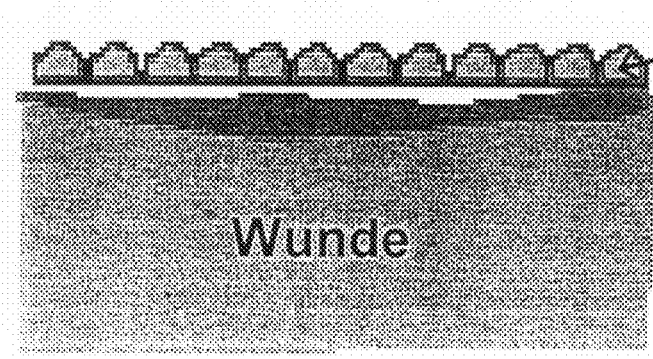
Fig. 3b

ARTIFICIAL "ARTERIO-VENOUS" PERMEABLE HOLLOW FIBER CAPILLARY SYSTEM

FIELD OF THE INVENTION

The invention relates, generally, to capillary wound dressings. More particularly, it relates to an artificial arteriovenous capillary membrane system including permeable, perfuseable hollow fibers.

DESCRIPTION OF THE PRIOR ART

While injuries to the upper layer of the skin (epidermis, keratinocytes) can regenerate by themselves most of the time, larger deeper wounds that reach the skin's regeneration layer (basal keratinocytes, progenitor cells) do not. The treatment of acute skin wounds, e.g. after burn injuries or chronic skin wounds, e.g. as a result of diabetes mellitus or peripheral circulatory disorders, is clinically not satisfactory.

Standard clinical therapy for larger skin wounds after wound cleaning is surgical autologous skin transplantation whereby a section of the patient's own healthy skin is surgically removed, followed by the preparation of a split skin-mesh transplant (where the to be transplanted skin is divided into a multitude of small areas), which is later transplanted on the wound area. However, autologous split-skin is often not available in sufficient amounts, thus having to depend on the wound's self-healing ability under the wound dressing.

The method of choice for chronic skin disease is to keep the wound moist/wet through regular misting and irrigating while the wound dressing is changed.

The purpose of the wound dressing in both applications is to reduce fluid- and temperature loss as well as infection.

More sophisticated wound dressings include for example Integra, Integra Life Science, USA or AlloDerm, LifeCell, USA, consisting of non-living, non-autologous cell cultures.

Methods for the removal of secretion from wounds are already known: Argenta, L. C., Morykwas, M. J. Vacuum assisted closure: A new method for wound control and treatment: Clinical experience. Annals of Plastic Surgery, 1997; 38(6): 563-77, or Joseph, E., et al.: A prospective randomized trial of vacuum assisted closure versus of chronic non-healing wounds; Wounds, 2000; 12(3): 60-7.

A device for keeping the wound moist is also commercially available as Wound V.A.C. Instill (Registered Trademark) from KCl, San Antonio, Tex., USA. This device can be employed to alternately supply the wound with fluids and subsequently alternately remove fluids from the wound. Here, mass transfer does not occur as it occurs in an artificial capillary bed, but with significant central and irregular gradients, via a shared inlet and outlet of a sponge in the center of the wound.

Carsin H. et al. and Phillips T. J. et al. and Still J. M. et al. published the early clinical results on keratinocyte transplantation.

The following are available commercialized skin replacements: Dermagraft-TC, by Advanced Tissue Sciences, USA, with live cells in form of sheets (extensive layers of connected cells), Organogenesis, USA, uses live human allogene fibroblasts and allogene keratinocyts in a two-layer arrangement that is marketed by Novartis, C H as Apligraf. Genzyme, USA offers a service where autologous keratinocytes are removed from an area of the patient's healthy skin and passaged in a culture dish, and then placed on the wound as live cell sheets using fat gauze as support structure. This method however, did not yield completely satisfactory clinical results. For example, blistering on the wound site lifts the cell sheets from the wound and significantly impairs cell supply in the wound.

For these currently established techniques, the wound supply is unsatisfactory during wound healing, or the attachment rate of applied cells. Problems include fluid-, electrolyte-, and pH displacements as well as bacteria accumulation in the wound.

Should transplanted cells be used, this non-physiologic biomatix in the wound also prevents optimal cell growth and cell proliferation.

Accordingly, what is needed is an improved, more effective device to facilitate the addition of treatment substances to and the excretion of waste from a skin wound. However, in view of the art considered as a whole at the time the present invention was made, it was not obvious to those of ordinary skill how the art could be advanced.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY OF THE INVENTION

The long-standing but heretofore unfulfilled need for an improved, more effective artificially capillary membrane system is now met by a new, useful and nonobvious invention.

The purpose of the invention at hand is to introduce a device that improves mass exchange in the wound, including during the initial clinical phase of possible cell transplantation. The method/device, however, is suitable as an active wound dressing even without adding cells. The device can perfuse and supply the wound in a decentral fashion during continuous perfusion and thus provides conditions similar to an arterio-venous capillary bed, and facilitates drug-, mediator-, growth factor-, and antibiotic/disinfectant perfusion, while enabling even substance distribution, and optionally the generation of moderate negative pressure. Likewise electrolyte- and pH-regulation can be performed in the wound and continuous debris removal can be enabled. A more open-porous arrangement enables a moist wound environment with the ability to remove wound debris and/or bacteria or other germs.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the nature and objects of the invention, reference should be made to the following detailed disclosure, taken in connection with the accompanying drawings, in which:

FIG. 1b depicts blister formation when using the prior art methods of FIG. 1a;

FIG. 2a depicts blister formation when using the prior art methods of FIG. 1a;

FIG. 3a depicts an application of cells individually sprayed onto a skin wound;

FIG. 3b depicts prior art methods used to apply in-vitro cultured cell sheets;

DETAILED DESCRIPTION OF THE PREFERRED EMBODIMENT

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

Figure 1A:
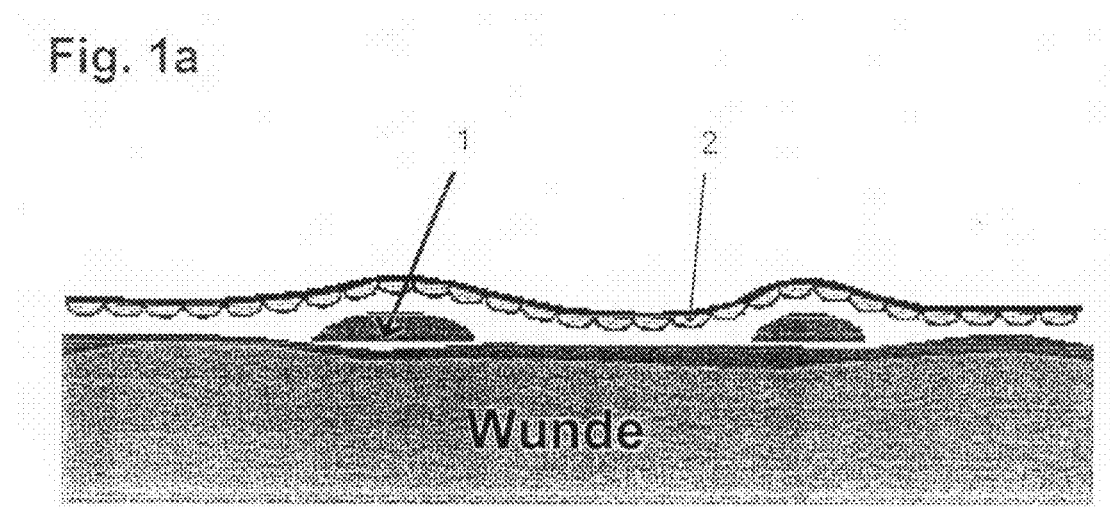
FIG. 1a depicts prior art methods used to apply in-vitro cultured cell sheets.
Figure 1B:
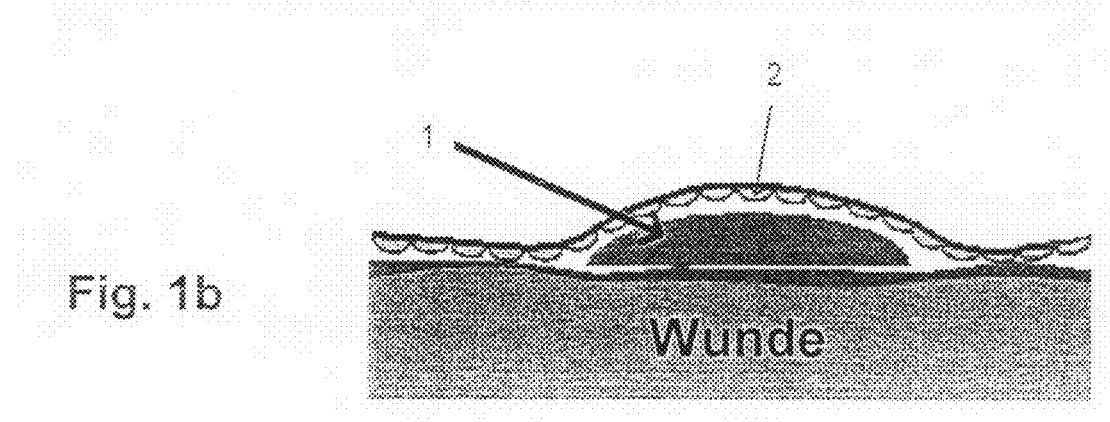

FIG. 1 depicts prior art clinical application of in-vitro cultured cells sheets causing problems due to blister development, in turn reducing the attachment rate of the cells. FIG. 1a depicts a schematic representation of the problem of clinical application of in-vitro propagated cell sheets 2 and the resulting blister development (see arrow 1). FIG. 1b shows how the blister (see arrow 1), expands during the attachment phase of the cell sheets 2 which negatively affects the adhering process of the cells to the skin. As a reference, the term "Wunde" is German for the term "Wound" in English.

Figure 2A:
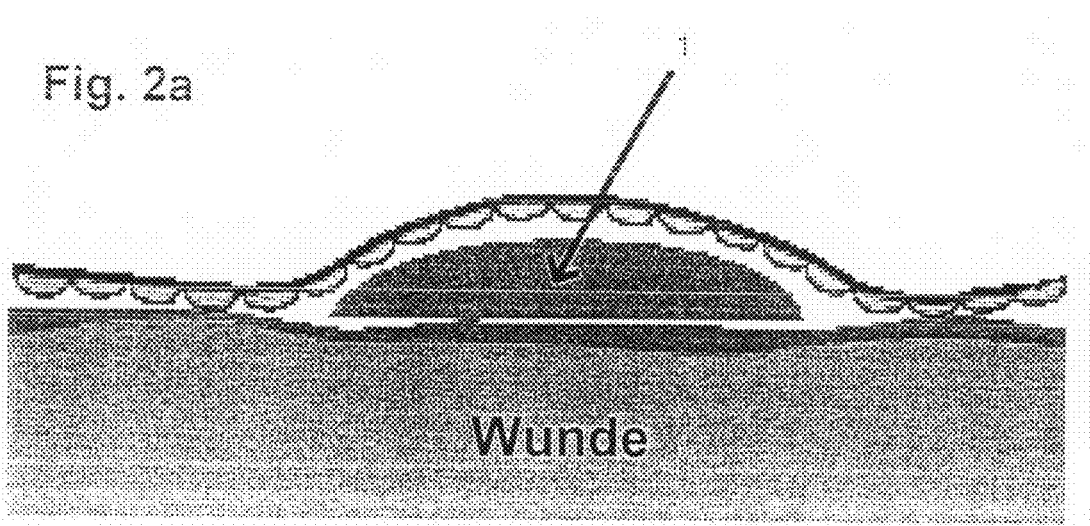
Figure 2B:
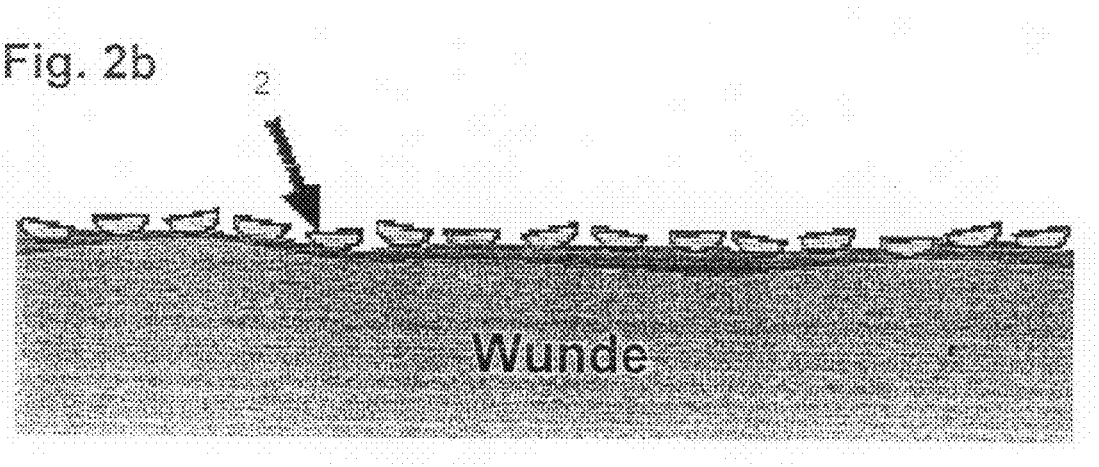
FIG. 2b depicts an application of cells individually sprayed onto a skin wound.

FIG. 2 depicts a schematic representation of cells individually sprayed onto the wound, thereby avoiding blister development and facilitating an improved healing process. FIG. 2a shows a design as it is shown in FIG. 1b with a blister (1), FIG. 2b shows the consequences when cells are sprayed onto the wound (the cells 2 are marked with an arrow). The comparison of FIGS. 2a and 2b demonstrates how blister development can be avoided by spraying the cells 2 onto the wound and thereby enabling improved wound healing. As a reference, the term "Wunde" is German for the term "Wound" in English.

FIG. 3 depicts a schematic representation of individual cells 2 sprayed onto the wound (FIG. 3a), which, in their function as progenitor cells, can heal significantly larger wound areas. FIGS. 3a and 3b show a schematic comparison with cell sheet 2 application (FIG. 3b). Using cell sheet application, cells are individually sprayed onto the wound, and as progenitor cells, a significantly larger wound area can be healed. The cells are marked by an arrow (2). As a reference, the term "Wunde" is German for the term "Wound" in English.

Figure 4:
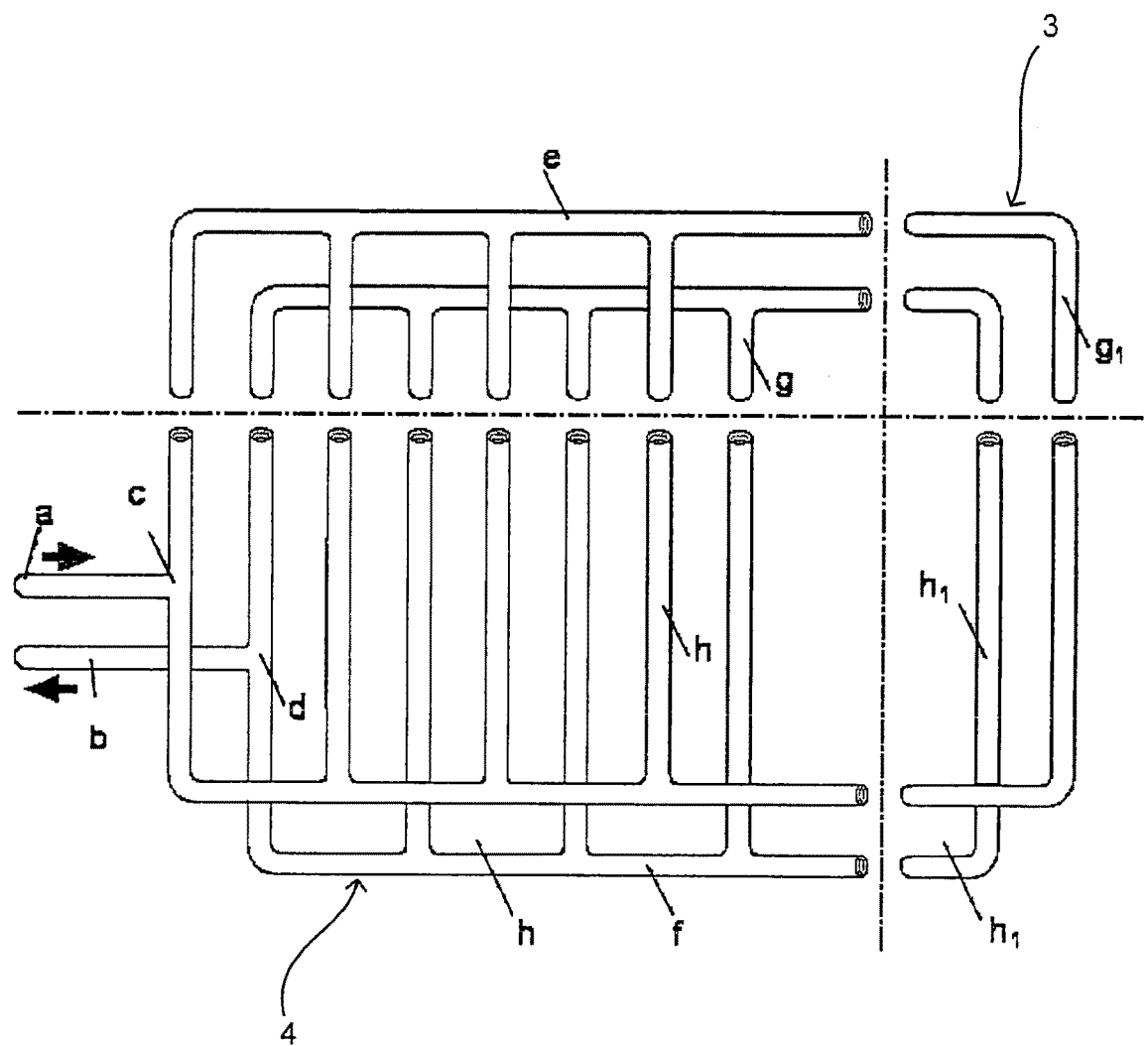
FIG. 4 depicts an artificial capillary membrane system with three compartments, i.e., two arrays of capillary membranes.

FIG. 4 depicts a schematic illustration of an artificial capillary membrane system that is connected to a surrounding that generates a first independent compartment (not shown, "wound" background), which depicts two additional hollow fiber arrangements generating the second independent compartment with capillaries c, e and h, and the third independent compartment with capillaries d, g and f. The second compartment (3) and the third compartment (4) are each equipped with one inlet or outlet and could perfuse the first compartment between the inlet of the second compartment and the outlet of the third compartment. The artificial capillary membrane system in FIG. 4 corresponds with the portion of the system depicted under the wound dressing shown in FIG. 5, which is located on top of the wound. The tube ends a and b with inflow and outflow arrows, respectively) in FIG. 4 correspond with the tube ends fin FIG. 6. The arrows in FIG. 7 correspond to point a and b in FIG. 4 respectively, or to tube ends f and f2 in FIG. 6, respectively. The capillary membrane system depicted in FIG. 4 corresponds also to the illustration in FIG. 8b.

Figure 5:
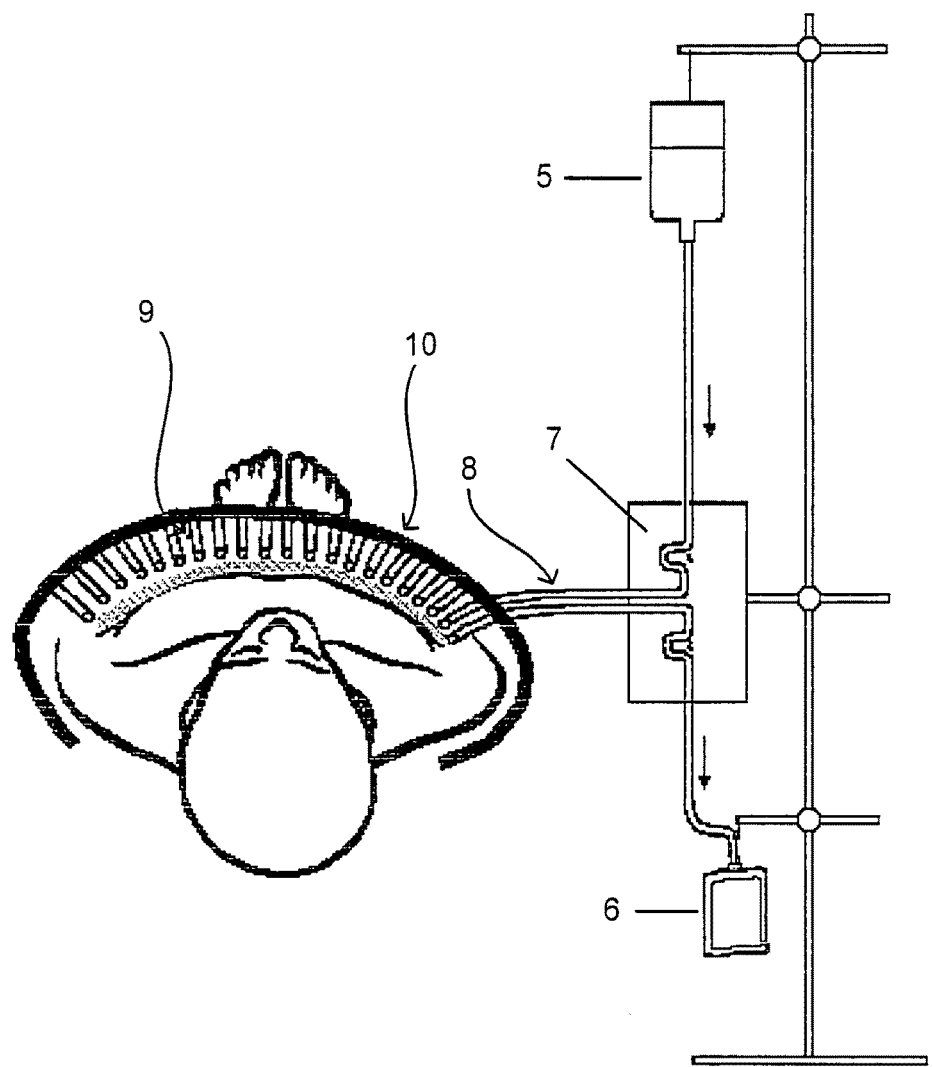
FIG. 5 depicts a schematic representation of the clinical application of an artificial capillary membrane system with pump circuit on a subject.

FIG. 5 depicts a clinical application of the artificial capillary system applied as active wound dressing (g, 10) with a fluid circulation system 8 and an infusion system, such as a pump system 7. Fluid is pumped from a reservoir 5 into a circuit (middle), a recirculation pump circulates the fluid to and from the capillary system 9 (shown in one arrangement in FIG. 4). A discharge pump pumps the fluids into an outlet reservoir 6. Negative or positive pressure can be generated in the wound compartment depending the speed settings of the top and bottom pump in pump system 7. Negative pressure enables additional removal of wound secretion and debris from the wound site.

Such an arrangement can also supply the wound in combination with sprayed cells (FIGS. 2 and 3) as well as support sprayed cells in the wound after spraying (FIG. 2).

Figure 7:
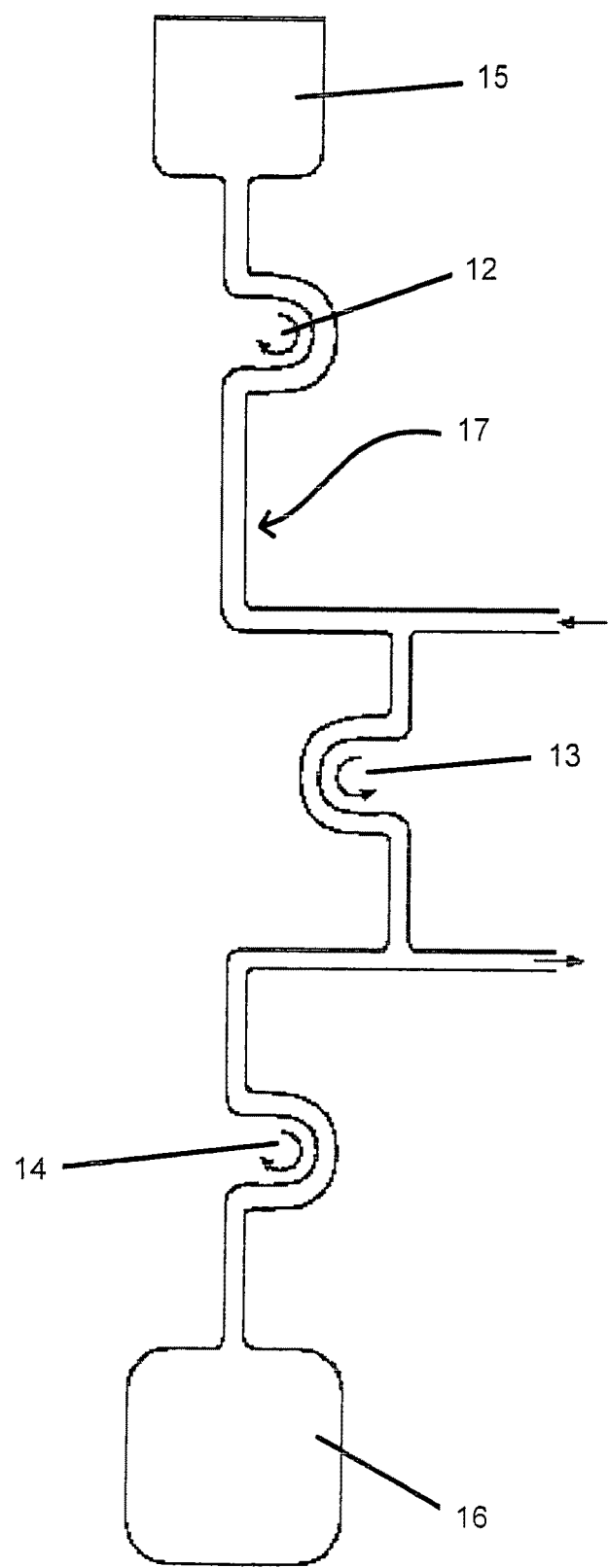
FIG. 7 depicts a pump circuit used in conjunction with an artificial capillary membrane system.

The tube system running through the pump system on the right side of the illustration is described in FIG. 7.

Figure 6:
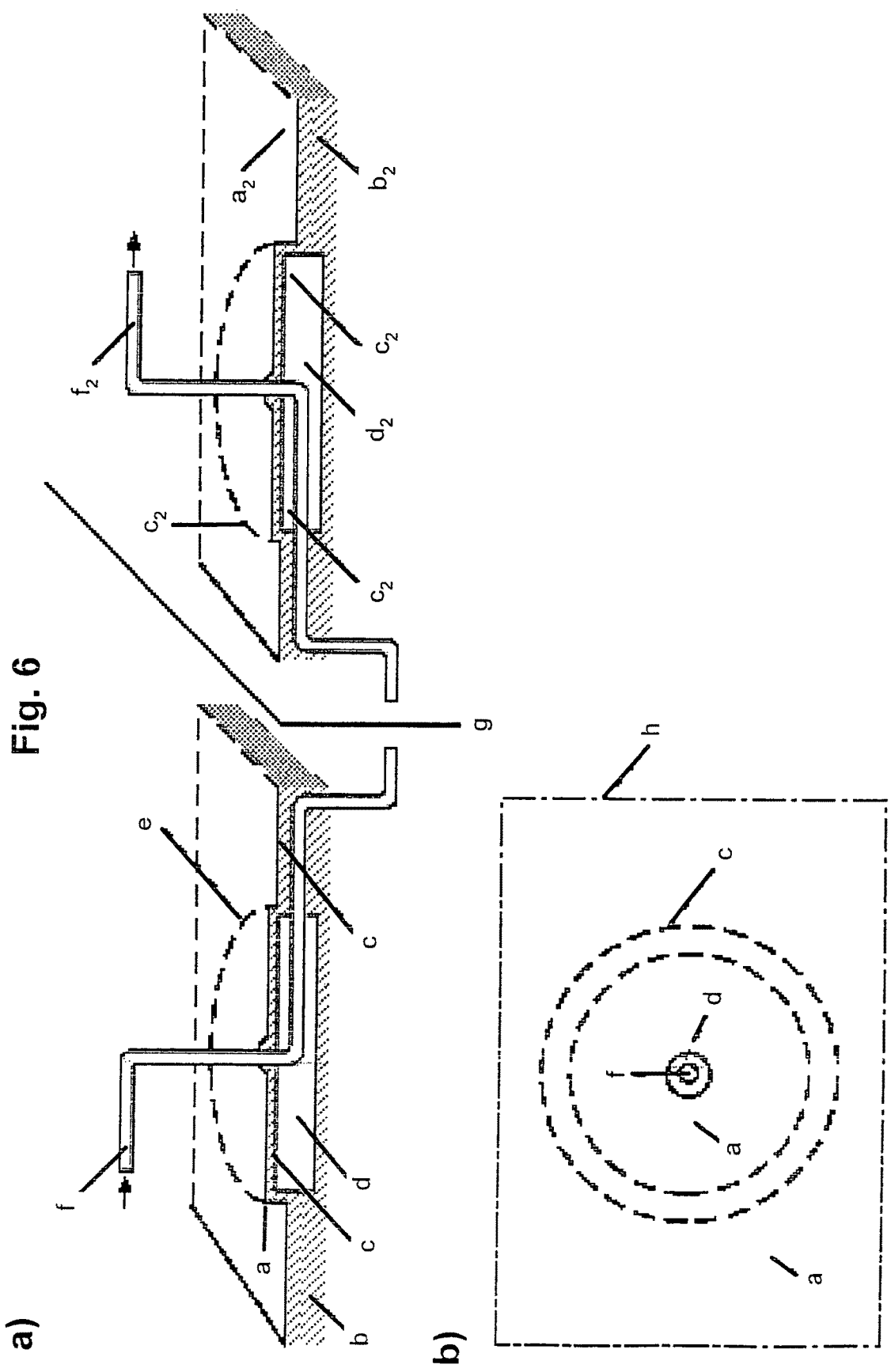
FIG. 6a depicts an inlet and outlet entering and exiting, respectively, a wound dressing and artificial capillary membrane system.
FIG. 6b depicts a cross-sectional view of an inlet containing a seal.

FIG. 6 depicts a particular arrangement of the tubes entering or exiting from the wound dressing, which enables sealing around tube between the skin b/b2 and the sheeting a/a2/h above wound and artificial capillary system. The tubes f/f2 exit from the wound b/b2 and a seal between the skin and the sheeting is enabled by the pad d/d2 above which the tube f/f2 exists the wound area through a hole c in the sheet a/h. The cut between FIG. 6a and FIG. 6b illustrates an inlet and outlet tubes a and b, respectively, in FIG. 4.

FIG. 7 depicts the tubes in an infusion system with three infusion inlets, such as pumps 12, 13, 14 to operate a hollow fiber membrane system circuit 17, as described in FIG. 4. This tube system is depicted in FIG. 5 in another arrangement. Fluid is pumped from a reservoir (15) into a circuit (17), a recirculation pump (13) circulates the fluid to- and from the capillary system (right side of illustration). The arrows correspond to a capillary system shown in one arrangement in FIG. 4. An outlet pump (14) pumps fluid into an outlet reservoir (16). The arrows in FIG. 7 can lead to inlet (a) and outlet (b) in FIG. 4 or to inlet (f) and outlet (f2) in FIG. 6. While the recirculation pump (13) controls the mass transfer from the circuit onto the wound, the top pump (12) and bottom pump (14) control the entire mass transfer from/to the patient. Negative or positive pressure can be generated in the wound compartment depending the speed setting of the top pump (12) and bottom pump (14). Negative pressure enables additional removal of wound secretion and debris from the wound site.

Figure 8:
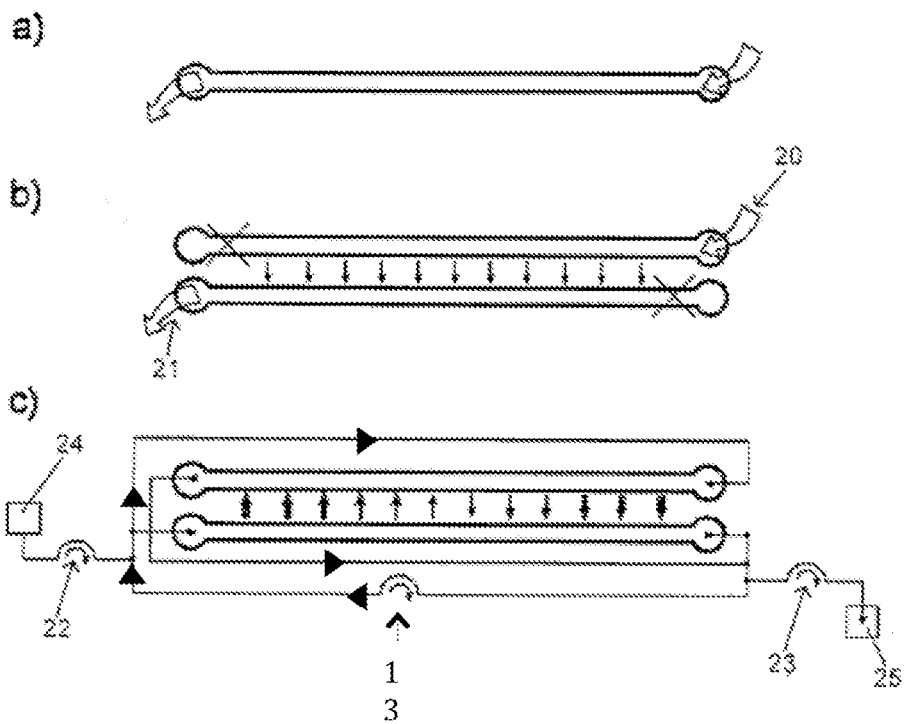
FIG. 8a depicts a two-compartment artificial capillary membrane system.
FIG. 8b depicts a three-compartment artificial capillary membrane system.
FIG. 8c depicts a three-compartment artificial capillary membrane system with a pump circuit.

FIG. 8 depicts three applications of the current invention. FIG. 8A depicts a two-compartment artificial capillary system, FIG. 8B depicts a three-compartment artificial capillary system, and FIG. 8C depicts the application of a three-compartment arterio-venous artificial capillary system that enables perfusion or counter current perfusion across the wound.

FIG. 8a depicts the illustration in FIG. 5; the configurations in FIG. 8c require a pump system whose circuit is illustrated in FIG. 7. While FIG. 8a) depicts a two-compartment system, FIG. 8b illustrates a three-compartment system; the first compartment is the wound area (not shown), the second compartment is the lumen of the upper capillary, and the third compartment is the lumen of the bottom capillary. In this arrangement, the second and third compartments are each equipped with an inlet (20) and outlet (21) that perfuse the first compartment between the inlet of the second compartment and the outlet of the third compartment. The arrows symbolize the counter current flow direction between the second and third compartments.

FIG. 8c also depicts the respective pumps (inlet pump 22 and outlet pump 23) as well as a medium inflow reservoir (24) and a medium outlet/waste reservoir (25).

Figure 9:
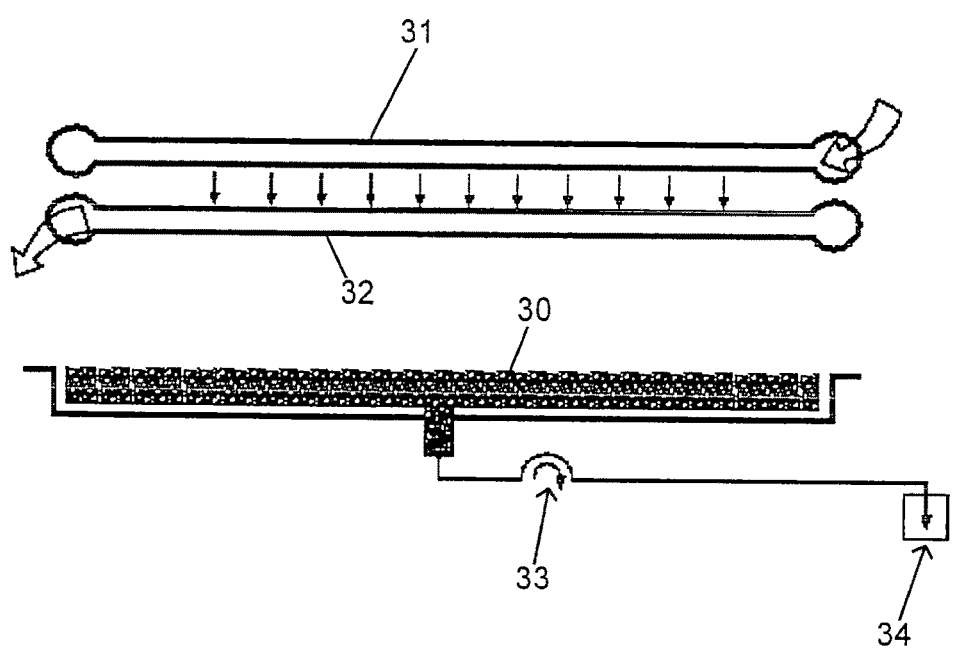
FIG. 9 depicts a three-compartment artificial capillary membrane system with a sponge and a pump circuit.

FIG. 9 depicts a schematic illustration of the combined application of a three-compartment "arterio-venous" artificial capillary system with hollow fiber capillary membranes (31, 32) that create a second and third independent compartment in the wound and a sponge (30) for additional and separate removal of fluids, substances, and/or bacteria out of the first compartment (i.e., wound space). The sponge enables additional and separate removal of fluids, substances, and/or bacteria via a separate pump (33) into separate waste reservoir (34). Here, mass transfer can be added by removing wound secretion and debris via the sponge.

In addition to mass transfer and the option to generate a negative pressure, as described in FIGS. 4, 7, 8b, 8c, negative pressure can also be generated in the wound, and/or wound secretion and debris can be additionally removed. This configuration is also of interest to be combined with two-compartment capillary systems.

The invention described here provides an artificial capillary hollow fiber membrane system that can be placed into a first surrounding that is creating an independent compartment, typically the wound environment, whereby the lumen of the artificial capillary system provides at least a second independent compartment and encompasses at least one perfuseable hollow fiber capillary membrane arrangement. It can include a second, or further, independently perfuseable hollow fiber capillary membrane arrangement that forms a third, or further, independent compartment. According to the invention, the at least one independent hollow fiber capillary membrane arrangement is assembled of 1 to 1000 hollow fibers, whereby the permeability limit is set for wound debris, and/or molecules of 500 to 2,000,000 MW cut off, preferably of 1,000 to 900,000 MW cut off. The number of capillary membranes in the membrane arrangements depends on the circumstances of the application and the connections, meaning whether an arrangement is built with many capillaries in parallel or fewer capillaries in a meandering course. If the capillary membranes are arranged in a meandering course, one single capillary can suffice, preferred are 1 to 100, preferably 1 to 50 and most preferred are 1 to 10 hollow fiber capillaries. When using a parallel arrangement, the number of hollow fibers can be larger, between 3 and 1000, preferably 5 to 600 and most preferred between 10 and 100 hollow fibers. Each hollow fiber capillary membrane arrangement consists of at least one inlet and at least one outlet. Combinations of parallel arrangements with meandering arrangements, and also duplication of several arrangements, which may be connected via main inflow and outflow tubes, are contemplated.

Because of the use of hollow fiber capillary membranes, the device can be arranged and operated on top of uneven contours of a body. Special capillary arrangement can be made for any region of a subject, for example hands, ears, or the face.

To ensure the optimal supply and waste removal for the cells, two independent hollow fiber capillary membrane arrangements may be included to form a second and a third independent compartment in the wound. It is critical for the artificial arterio-venous permeable hollow fiber capillary system that even- and continuous mass transfer is provided between the first independent compartment, which forms the wound surroundings and at least one of further compartments. If a one-compartment hydrophilic capillary system is used, the flow is from the inlet to the outlet; if a two-compartment system is used, the flow is typically in counter-current flow between two inlets and two outlets. Further compartments can add further functions, for example gas flow in a hydrophobic oxygenation compartment. Even mass distribution is important for optimal supply of the wound, including spray-transplantation of skin cells into the wound, as well as the removal of secretion, fluids and/or debris out of the wound. In smaller wound systems, even and continuous mass transfer can be enabled by one capillary compartment. Even distribution in larger wounds can be enabled by two capillary compartments. Every system resembles the functions of the arterial and venous capillaries in the natural tissue.

The inner diameter of the hollow fibers is preferably between 10 µm and 2000 µm, most preferably between 40 µm and 800 µm.

According to the invention, other design forms are included in which additional hollow fiber capillary membrane arrangements forming independent compartments can be instituted, e.g. for wound oxygenation. In the case where several independent hollow fiber capillary membrane arrangements are utilized, each individual hollow fiber capillary membrane can have one inlet and at least one outlet available or, some independent compartments can share one inlet and one outlet.

With respect to materials and regarding the hollow fibers of the hollow fiber capillary membrane arrangements, the invention at hand may contain any known natural or synthetic polymers or porous ceramics that are used for hollow fibers (for example cellulose, polysulfone, polyethersulfone, polyamide or other synthetic or natural polymers), absorbable/degradable biomaterials, (including collagen and/or digestible cellulose), known in medical hollow fiber membrane technology, individually or in combination.

Because of the arrangement of hollow fiber capillary membranes with central inlets and outlets, the invention can be applied under a sterile wound dressing, e.g. skin wound dressing in form of a water impermeable foil, as known from surgical operation procedures. This preferred embodiment allows the holding of the fluids in the wound.

With the invention at hand perfusion of solutions in the wound is enabled. These solutions include physiologic electrolytes solutions (such as saline and buffer), nutrition (such as sugars and amino acids), drugs, antibiotics, growth factors, mediators, regeneration factors, dialysate solutions, irrigation solutions, among other suitable solutions that help treat skin wounds.

To support the perfusion via the inlet and outlets, the invention at hand is equipped with at least one tube perfusion system—preferably disposable—with a fluid supply bottle/bag and waste bottle/bag, operated by various forces, for example mechanical manipulation or gravity. Preferably, the tube system is operated by a pump device, for example a roller pump device, for sterile disposable pump tubes. If one of the capillary compartments serves as oxygenator, the applicable inlet or outlet is connected to at least one gas supply. It is particularly advantageous to apply fluid medium inlet pumps, medium outlet pumps and/or medium circulation pumps, which can all be applied individually or in combination.

By means of the afore described modification of the invention at hand it is possible to arrange and operate the device in open perfusion mode. The invention at hand can also be arranged and operated in recirculation mode with a medium inlet shank and medium outlet shank. The described device can alternatively be operated in counter current flow mode when the appropriate pump devices are installed.

The invention at hand can be further modified in such a way that the hollow fiber capillary membrane arrangement forming at least one independent compartment is, in addition, equipped with a pressure control device, and/or flow control, and/or malfunction switch, and/or medium warmer, and/or medium oxygenation, and/or probes for pressure, flow, $PO_2$, $CO_2$, Temperature, pH, electrolytes, glucose, lactate and/or corresponding regulation units.

To support the suction of secretion, fluids, and/or debris it is also possible to apply the invention at hand under a sterile wound dressing in combination with a sponge connected to a suction system. Thus, the secretion, fluids, and/or debris can be removed, in addition or separately, from the capillary compartments.

The hollow fiber capillary membrane arrangement can also be applied in a soft tissue wound as well as in the abdomen. In such a case, the hollow fiber capillary membrane arrangement can also be operated in combination with a sponge, which is equipped with an additional suction tube for the removal of secretion, fluids, and/or debris.

It is advantageous if in addition to the capillary membranes, skin cells are applied prior to and/or during the wound treatment (FIGS. 2,3). In this case the invention at hand supports treatment of skin defects with cells since cell supply can be enabled by the perfusate flowing through the capillary membrane system. The skin cells can be applied via a cell suspension through a spray head, for example the device disclosed in patent application Ser. No. 11/518,012. The advantage of this is that the cells can be evenly distributed across a larger area through the spray head, thereby enabling a larger transplant area (FIG. 2b). Especially through the use of skin progenitor cells or stem cells, this combination yields a significant enlargement of the possible therapeutic wound area (FIG. 3a). Using the invention at hand, cells can be temporarily supplied via the hollow fiber capillary membrane arrangement.

The combination of the afore described cell spray method with the capillary system according to the invention has multiple advantages compared to the prior art technology. These advantages include confluent growing cells dividing less, starting proliferation later after transplantation, and exhibiting less cell migration activity. The combination has the advantage that the number of in-vitro passages can be reduced. Thus, cells expanded in-vitro can be applied earlier, reducing passage umbers and unwanted differentiation of basal keratinocytes (or skin progenitor cells) to keratinocytes. An even earlier therapy can be enabled by spraying intraoperative isolated skin cells, isolated and applied during the same operation, with the combination of the artificial capillary membranes. By avoiding in vitro culture, the basal keratinocytes cannot differentiate and, at the same time, due to the improved supply via the artificial capillaries the attachment and the supply of the cells that were temporarily impaired by the isolation process, can be supported by fluid exchange in the wound. In a preferred method, the artificial capillaries facilitate temporary support to the sprayed cells between the wound and the outer wound dressing during the first treatment days. Nutrients, tempering, oxygenation, pH-regulation, electrolyte exchange, or detoxification as well as growth factors or antibiotics can also be applied.

Artificial capillaries were built—according to FIG. 4—in five versions: one in a 20×20 mm outer dimension "mat", one in a 40×40 mm outer dimension "mat", one in a 40×80 mm outer dimension "mat", one in a 40×120 mm outer dimension "mat", and one in a 200×400 mm outer dimension "mat". In each mat, hollow fiber capillaries of less than one millimeter in outer diameter (medical grade microporous polyether sulfone plasma separation membranes, mPES, Akzo Membrana, Wuppertal, Germany) with a permeability limit for molecules of approximately 200,000 MW cut-off were arranged in parallel, with 5 capillaries per running 10 millimeters of a "mat". Thereby the 20×20 millimeter "mat", for example, contained 10 parallel arranged capillaries of 20 millimeter length each. All ends of fibers on one side of the mat were glued (Silastic, Dow Corning, USA) into silicone rubber tubes (Dow Corning, USA) having 2 millimeter inner diameters, where previously small holes were punched for each matching point. Each capillary and each tube remained perfuseable after gluing. Thereby, each "mat" has an inflow tube system on one side and a tube outflow system on an opposite side, and the tubes represent common inflow or outflow distribution tubes for all fibers (arranged in parallel) in the "mat". Two of these "mats" where overlaid and thus formed an "arterial-venous" capillary system. In each of those arrangements (containing two overlaid mats), each "mat" represents the lumen of one independent artificial capillary system, the first "mat" providing a second compartment and the second "mat" providing a third independent perfuseable compartment.

The flexibility of the capillary arrangement allowed an easy placement of the artificial capillary membrane system on body contours.

With the placement of hollow fiber capillary membranes under a foil, a water impermeable surgical operation wound incision foil, and the use of silicone rubber (Silastic, Dow Corning, USA) plates as described in FIG. 6, the device could be sealed onto the skin and covered by a skin wound dressing. This arrangement allows the holding of fluids in the compartment between artificial capillaries and the skin and under the wound dressing.

To support the perfusion via the inlet and/or outlets, the device was connected via Luer-lock connectors (out of polystyrol) to a tube perfusion system (poly-vinyl chloride, PVC, tubing), with a Luer-lock infusion solution bag and a Luer- Lock waste container bag, as depicted in FIG. 7, and operated as depicted in FIGS. 5 and 8c) with standard infusion tube roller pumps.

It will thus be seen that the objects set forth above, and those made apparent from the foregoing disclosure, are efficiently attained. Since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

The invention claimed is:

1. An artificial capillary membrane system adapted to simulate an capillary bed for the treatment of a skin wound on a subject, comprising:
    a first flexible array of hollow fiber capillaries comprising a plurality of perfusable hollow fiber capillaries arranged in parallel, wherein at least one end of these hollow fiber capillaries inserts into the lumen of a tube that connects these parallel hollow fiber capillaries;
    a second flexible array of hollow fiber capillaries comprising a plurality of perfusable hollow fiber capillaries arranged in parallel, wherein at least one end of these hollow fiber capillaries inserts into the lumen of a tube that connects these parallel hollow fiber capillaries;
    wherein the hollow fiber capillaries of the first and second array have a plurality of pores which are capable of mass transfer with the material inside the wound,
    wherein the first and second arrays each have at least one channel adapted as an inlet or an outlet, and
    wherein the first and second arrays are placed on or in a wound and arranged to created the following compartments:
        a) a first compartment formed between the outside of the arrays and the surrounding wound;
        b) a second compartment defined by the lumens of the hollow fiber capillaries of the first array; and
        c) a third compartment defined by the lumens of the hollow fiber capillaries of the second array.

2. The artificial capillary membrane system of claim 1, wherein the each hollow fiber capillary has an internal diameter between 40 µm and about 800 µm.

3. The artificial capillary membrane system of claim 1, wherein the each hollow fiber capillary includes material selected from the group consisting of modified cellulose, polysulfone, polyethersulfone, and polyamide.

4. The artificial capillary membrane system of claim 1, further comprising living cells disposed within said system, whereby the cells can be applied to the skin wound.

5. The artificial capillary membrane system of claim 4, wherein the living cells are autologous stem cells.

6. The artificial capillary membrane system of claim 1, further comprising a seal disposed between the skin of the subject and the first array of hollow fiber capillaries.

7. The artificial capillary membrane system of claim 1, further comprising a pump circuit which includes at least one infusion inlet and at least one reservoir in open communication with the first array of hollow fiber capillaries, whereby the pump circuit has a configuration to create a negative pressure to enable additional removal of wound secretion and debris from the skin wound.

8. The artificial capillary membrane system of claim 7, wherein the at least one infusion inlet includes an inlet pump, an outlet pump, and a recirculation pump.

9. The artificial capillary membrane system of claim 7, wherein the at least one reservoir includes an inflow reservoir and a waste reservoir.

10. The artificial capillary membrane system of claim 1, further comprising a sponge disposed between the first array of hollow fiber capillaries and the at least one infusion inlet, whereby the sponge enables additional removal of waste excreted from the skin wound.

11. The artificial capillary membrane system of claim 1, wherein the first array has a permeability cutoff of about 500 Da.

12. The artificial capillary membrane system of claim 1, wherein the first array has a permeability cutoff of wound debris up to about three millimeters in diameter.

13. The artificial capillary membrane system of claim 1, wherein the second array has a permeability cutoff of about 1,000 Da to about 50,000 Da.

14. The artificial capillary membrane system of claim 1, wherein the first array of hollow fiber capillaries includes between about ten and about one hundred hollow fiber capillaries.

15. The artificial capillary membrane system of claim 1, wherein the first array of hollow fiber capillaries includes between about one and about ten hollow fiber capillaries.

16. The artificial capillary membrane system of claim 1, further comprising a medium inlet shank and a medium outlet shank, whereby the system can be arranged and operated in a recirculation mode.

17. An artificial capillary membrane system adapted to simulate an arterio-venous capillary bed for the treatment of a skin wound on a subject, comprising:
    a first flexible array of hollow fiber capillaries comprising a plurality of perfusable hollow fiber capillaries arranged in parallel, wherein at least one end of these hollow fiber capillaries inserts into the lumen of a tube that connects these parallel hollow fiber capillaries;
    a second flexible array of hollow fiber capillaries comprising a plurality of perfusable hollow fiber capillaries arranged in parallel, wherein at least one end of these hollow fiber capillaries inserts into the lumen of a tube that connects these parallel hollow fiber capillaries;
    wherein the hollow fiber capillaries of the first and second array have a plurality of pores which are capable of mass transfer with the material inside the wound,
    wherein the flexible first array of hollow fiber capillaries defines a first compartment between the skin wound and the outside of the array, and a second compartment within the lumens of the hollow fiber capillaries, wherein these hollow fiber capillaries have a permeability cutoff of about 500 Da;
    wherein the flexible second array of hollow fiber capillaries is operational in a counter current flow mode, defines a third compartment within the lumens of the hollow fiber capillaries, wherein these hollow fiber capillaries have a permeability cutoff of about 1,000 Da to about 50,000 Da;
    the hollow fiber capillaries within the first and second array have an outer diameter of less than one millimeter, wherein each array includes between about ten and about one hundred hollow fiber capillaries in a parallel arrangement;
    each hollow fiber capillary from the first and second arrays of have a plurality of pores and an internal diameter between about 40 µm and about 800 µm each hollow fiber capillary includes materials selected from the group consisting of modified cellulose, polysulfone, polyethersulfone, and polyamide;
the first array of hollow fiber capillaries have at least one channel adapted for an inlet or an outlet;
the second array of hollow fiber capillaries have at least one channel adapted for an inlet or an outlet;
autologous stem cells disposed within the hollow fiber capillaries, whereby the stem cells can be applied to the skin wound;
a seal disposed between the skin of the subject and the first array of hollow fiber capillaries;
a pump circuit including an inlet pump, an outlet pump, a recirculation pump, an inflow reservoir and a waste reservoir,
the pump circuit being in open communication with the first and second arrays, whereby the pump circuit has a configuration to create a negative pressure to enable additional removal of wound secretion and debris from the skin wound;
a sponge disposed between the first array and the pump circuit, whereby the sponge enables additional removal of waste excreted from the skin wound; and
a medium inlet shank and a medium outlet shank, whereby the artificial capillary membrane system can be arranged and operated in a recirculation mode.

\* \* \* \* \*